(12) United States Patent
Vezinet et al.

(10) Patent No.: US 10,690,710 B2
(45) Date of Patent: Jun. 23, 2020

(54) METHOD FOR PREPARING AN OBJECT TO BE TESTED AND METHOD FOR IMPROVING THE UNIFORMITY AND INTENSITY OF AN ELECTRIC FIELD INDUCED IN SAID OBJECT ILLUMINATED BY AN INCIDENT ELECTROMAGNETIC WAVE

(71) Applicant: COMMISSARIAT A L'ENERGIE ATOMIQUE ET AUX ENERGIES ALTERNATIVES, Paris (FR)

(72) Inventors: Rene Vezinet, Bio (FR); Alexandre Catrain, Le Vigan (FR); Thomas Chretienot, Gramat (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 549 days.

(21) Appl. No.: 15/312,867

(22) PCT Filed: May 27, 2015

(86) PCT No.: PCT/EP2015/061758
§ 371 (c)(1),
(2) Date: Nov. 21, 2016

(87) PCT Pub. No.: WO2015/181258
PCT Pub. Date: Dec. 3, 2015

(65) Prior Publication Data
US 2017/0184648 A1 Jun. 29, 2017

(30) Foreign Application Priority Data

May 28, 2014 (FR) ...................... 14 54821

(51) Int. Cl.
*G01R 29/08* (2006.01)
*G01N 1/28* (2006.01)
(Continued)

(52) U.S. Cl.
CPC .......... *G01R 29/0828* (2013.01); *G01N 1/28* (2013.01); *G01N 1/44* (2013.01); *G01N 22/00* (2013.01); *G01N 33/4833* (2013.01)

(58) Field of Classification Search
None
See application file for complete search history.

(56) References Cited

U.S. PATENT DOCUMENTS 5,748,002 A * 5/1998 Scott ...................... G01N 22/00
324/633
2001/0050810 A1 12/2001 Lorincz
(Continued)

OTHER PUBLICATIONS

International Search Report dated Jun. 25, 2015, in PCT/EP2015/061758, filed May 27, 2015.
(Continued)

*Primary Examiner* — Jermele M Hollington
*Assistant Examiner* — Suresh K Rajaputra
(74) *Attorney, Agent, or Firm* — Oblon, McClelland, Maier & Neustadt, L.L.P.

(57) ABSTRACT

A method for preparing an object to be tested, having a given relative permittivity, intended to be illuminated by an incident electromagnetic wave. The method includes: providing a part including a cavity for housing the object and at least one extension element made from a material having a relative permittivity that is preferably equal to that of the object, the extension element at least partially delimiting the cavity and extending to either side of the cavity in a passage direction of the cavity, over a length at least equal, on either side of the cavity, to one third of the length of the cavity in (Continued)

the passage direction, and placing the object in the cavity, such that the object is in contact with the extension element in the passage direction.

20 Claims, 5 Drawing Sheets

(51) Int. Cl.
    *G01N 22/00*     (2006.01)
    *G01N 1/44*     (2006.01)
    *G01N 33/483*     (2006.01)

(56) References Cited

U.S. PATENT DOCUMENTS

2005/0215020 A1\*   9/2005   Bergstedt .............. H01P 11/008
                                                      438/309
2018/0076502 A1\*   3/2018   Chretiennot .............. H01P 5/08

OTHER PUBLICATIONS

French Search Report dated Jan. 26, 2015, in French Patent Application No. 1454821, filed May 28, 2014.

International Preliminary Report on Patentability dated Jul. 8, 2016, in PCT/EP2015/061758, filed May 27, 2015.

Laval, et al. "A New In Vitro Exposure Device for the Mobile Frequency of 900 MHz", Bioelectromagnetics vol. 21, 2000, 9 pages.

Schuderer, et al. "In Vitro Exposure Systems for RF Exposures at 900 MHz", IEEE Transactions on Microwave Theory and Techniques, vol. 52, No. 8, XP-001200626, Aug. 2004, 9 pages.

Angulo, et al., Improving the SAR Distribution in Petri-Dish Cell Cultures, Journal of Electromagnetic Waves and Applications, vol. 24, XP55164688, 2010, 14 pages.

Fontana, et al., "On the Influence of a Glas Slide on the SAR Distribution in Petri Dishes for In Vitro Exposure to 2.45 GHz EM Fields", Antennas and propagation society international symposium (APSURSI), 2010, 4 pages.

U.S. Appl. No. 14/648,977, filed Jun. 2, 2015, US 2015/0299640, Rene Vezinet et al.

\* cited by examiner

METHOD FOR PREPARING AN OBJECT TO BE TESTED AND METHOD FOR IMPROVING THE UNIFORMITY AND INTENSITY OF AN ELECTRIC FIELD INDUCED IN SAID OBJECT ILLUMINATED BY AN INCIDENT ELECTROMAGNETIC WAVE

TECHNICAL DOMAIN

The domain of the invention is electromagnetism and bioelectromagnetism. The invention is particularly applicable in the field of dosimetric characterisation of an object to be tested when this object is illuminated by an incident electromagnetic wave in free space or in an exposure system for experimental purposes, to study interactions between electromagnetic waves and living tissues.

State of Prior Art

The purpose of studies carried out in the field of bioelectricity and by extension bio-electromagnetism, is to study the effects of electromagnetic fields on living tissues. These studies require experimental systems capable of exposing, to electromagnetic fields, various biological or chemical organisms of varying sizes and natures ranging from a molecule or cell to complete organisms (plants, mice, etc.).

It may consist of studies for standardisation purposes applicable to the determination of harmfulness and harmlessness thresholds (telephony, transmissions, electromagnetic defense applications, electrical equipment, etc.), for medical purposes (treatment of cancer, neural stimulation, etc.), or industrial purposes (decontamination, sterilisation, food transformation processes, etc.).

These experimental studies make use of exposure systems that must perform a support function for objects under test during phases of illumination by an electromagnetic field; in general, they must also act as a container, since the objects to be tested are usually in liquid form. For example, it might be required to consider the exposure of microscopically sized biological objects such as cells, GUV (Giant Unilamellar Vesicles) or spheroids, that are usually in suspension in a biological medium (solution with low electrical resistivity). The most frequently used containers are cylindrical in shape, and may be Eppendorf™ tubes, Petri boxes or other types.

Many experimental exposure systems are used at the present time, such as "plane wave" type exposure systems, reverberating rooms (CRBM), wave guides (cylindrical or rectangular), wire patch cells, radial transmission lines or transmission lines with plane conductors, for example such as TEM (Transverse Electro Magnetic) cells.

The disadvantage of these systems is that the uniformity of the incident electromagnetic field is more or less good depending on the exposure system used.

Furthermore, even in the ideal case of plane wave exposure (illumination by a distant antenna in free space) for which the uniformity of the incident field is perfect, it is found that the uniformity and intensity of the electric field induced in the volume of the object under test depend on the nature and the geometry of the object under test and the polarisation and angle of incidence of the incident wave.

However, it is essential to achieve very good uniformity of the field within the volume of the OUT and to have a good coupling factor (intensity of the induced field/incident field) and to have perfect control over fields penetrating into the volumes of objects under test to guarantee the validation and reproducibility of experiments

PRESENTATION OF THE INVENTION

The main purpose of the invention is to improve the uniformity and to increase the intensity of an electric field induced in an object under test exposed to an incident electric field.

To achieve this, the invention discloses a method for preparation of an object to be tested that will be illuminated by an incident electromagnetic wave, the object having a given relative permittivity, wherein the method comprises:

supply of a part having a cavity for housing the object and at least one extension element made of a material with a relative permittivity equal to the relative permittivity of the object within +/−50%, said at least one extension element partly delimiting the cavity and extending on each side of the cavity along a direction said to be the passage direction of the cavity, over a length which is, on each side of the cavity, equal to at least one third of the length of the cavity along the passage direction; and placement of the object in the cavity such that the object is in contact with said at least one extension element along the passage direction.

Advantageously, an extension element has a relative permittivity equal to the relative permittivity of the object within +/−40%, and preferably within +/−30%, even more preferably within +/−25%, even more preferably within +/−20% and even more preferably within +/−10%. Preferably, if there are several extension elements, the chosen extension elements shall have the same relative permittivity. In fact the efficiency of the method according to the invention is maximum when the relative permittivity of the extension element(s) is (are) equal to that of the object and degrades with increasing difference between the relative permittivities of the object and the extension element(s).

Preferably, the relative permittivity of an extension element is equal to the relative permittivity of the object.

According to one preferred embodiment, the object to be tested has a given electrical conductivity and the electrical conductivity of said at least one extension element is equal to that of the object within +/−30%, preferably within +/−25%, even more preferably within +/−20% and even more preferably within +/−10%. Note that it is quite possible to use one or several extension elements made of a material with a zero or very low electrical conductivity. However, the method is more efficient if the extension material is chosen to have an electrically conductivity similar to or ideally equal to that of the object. Preferably, if there are several extension elements, the extension elements chosen are made of the same material so that they will have the same relative permittivity and the same electrical conductivity.

According to a first variant, the part comprises a support device and said at least one extension element is a layer deposited on a surface of the support device, a well being made in said layer to form the cavity in which the object is to be housed. For example, the support device might be a plate, for example a glass slide for a microscope, or a container such as a Petri box.

According to a second variant, said at least one extension element is a layer, a non-through well being made in said layer to form the cavity in which the object is to be housed. This layer may possibly be deposited on a support device (plate or Petri box).

According to a third variant, said at least one extension element is a block comprising a closed cavity that forms the cavity in which the object is to be housed.

According to a fourth variant, the part comprises a hollow support device with two opposite ends connected by a wall and said at least one extension element is a first layer closing off one of the two ends of the hollow support device and a second layer closing off the other one of the two ends of the hollow support device, the space delimited by the wall and the first and second layers forming the cavity in which the object is to be housed. The support may for example be an Eppendorf™ type tube. Preferably, the first and second layers are made of the same material.

Preferably, the cavity in which the object is to be housed in the above variants is a cylinder with a variable height (Petri box, Eppendorf™ tube, etc.). Cylindrical shapes are frequently used by biologists (Petri boxes, Eppendorf™ tubes, etc.). The cylindrical geometry of the well also has the advantage that it prevents reinforcement of fields at sharp-cornered parts that could have a less regular geometry.

According to the particular embodiments, the length of an extension element on each side of the cavity is equal to at least half, and preferably equal to at least the length, and even more preferably equal to at least twice the length of the cavity along the passage direction.

The invention also concerns a method for improving the uniformity and intensity of the electric field induced in an object to be tested illuminated by an electromagnetic wave, said method comprising:

preparation of the object to be tested using the preparation method described above; and application of an electric field on the object to be tested by illumination of the object with an incident electromagnetic wave, the direction of the electric field of the incident electromagnetic wave being chosen to be identical to the passage direction of the cavity. The improvement method according to the invention may be used in free space.

According to one embodiment of the improvement method according to the invention for use in guided space, the preparation step of the object to be tested further includes placement of the part in an exposure system having a hollow electrically conducting element made of an electrically conducting material extending along a longitudinal direction and having two electrically conducting portions facing each other in a section plane along a longitudinal direction, the part being placed in the hollow element between the two electrically conducting portions of the hollow element. Preferably, the part is positioned such that the passage direction of the cavity of the part is perpendicular to the longitudinal direction of the hollow element. The exposure system may for example be a waveguide with a square, rectangular or cylindrical section.

According to another preferred embodiment of the method of improvement according to the invention for use in guided space, the step in which the object to be tested is prepared further comprises placement of the part in an exposure system having at least two electrically conducting elements made of an electrically conducting material and placed approximately parallel to and facing each other (the two electrical conduction elements may be oblique, but are preferably parallel) such that the part is placed between the two electrical conducting elements. Preferably, the part is positioned such that the passage direction of the cavity of the part is perpendicular to the two electrical conducting elements. The exposure system may for example be a transmission line having at least two electrical conductors, for example a TEM cell.

In both of these embodiments, the assembly formed by the object to be tested, said at least one extension element and possibly the support device, if there is one, is installed respectively between two electrically conducting portions or between two electric conduction elements. Preferably, said at least one extension element of the part is in contact with one of the two electrically conducting portions and preferably with both electrically conducting portions, or with one of the two electrically conducting elements and preferably with both electrically conducting elements The configurations in which the extension material is in contact with the two electrically conducting portions or with the two electrically conducting elements prevent a non-uniform distribution of the electrical field between the extension material and the empty space. These configurations assure uniformity and maximum intensity of the electrical field of the object under test. In other words, these configurations in which the extension element is in contact with the two conductors that form a guided wave structure (for example a two-conductor wire, a TEM cell, etc.) guarantee a maximum coupling factor of the electrical field with the sample under test, and perfect uniformity of the electrical field in this sample. In devices according to prior art, there is an air space between the sample and the electrical conductors. This is the case for example of the classical case of a Petri box located between the two electrically conducting plates of a TEM cell. The presence of this air space between the sample and the electrical conductors results in a reinforcement of the electric field in this air space, to the detriment of the coupled electric field in the sample. This is explained by the large difference in dielectric permittivities of the sample (usually an aqueous liquid solution) and air. The coupling factor is strongly reduced and there is a steep gradient at the solution/air interface. This clearly illustrates the benefit in having contact between the extension element and at least one of the conducting contacts, preferably between the extension element and the two conducting contacts.

This invention consists of artificially modifying the geometry of the object under test by prolonging its dimensions in at least one direction (the direction of the incident electric field) by placing the object to be tested in contact with a material with electrical characteristics (relative permittivity and electrical conductivity) similar to its own. This maximises the coupling ratio between the electric field induced in the volume of the object under test and the incident electric field, which has the effect of increasing the intensity of the induced electric field; this also increases the uniformity of the induced electric field in the volume of the object under test.

This invention can be applied to the field of bio-electromagnetism. In particular, it can be used during experiments that make use of biological or chemical objects and is particularly suitable for objects under test in liquid form.

The invention can be used during illumination experiments in free space, in front of a radiating antenna or inside some known exposure systems (for example such as TEM cells).

Note that determination of the electric field induced in the object under test may be facilitated by the method according to the invention. The induced electric field can be measured using an appropriate sensor that would be placed in the volume of the object to be tested. The position of the sensor in the extension material close to the object to be tested makes it possible to obtain an estimate of the induced electrical field without any physical contact with the object, which is particularly beneficial (no pollution of the sensor, object under test not disturbed by the sensor).

Other advantages and characteristics of the invention will become clear after reading the following detailed non-limitative description.

BRIEF DESCRIPTION OF THE DRAWINGS

This description will be made with reference to the appended drawings among which.

DETAILED PRESENTATION OF PARTICULAR EMBODIMENTS

Figure 1A:
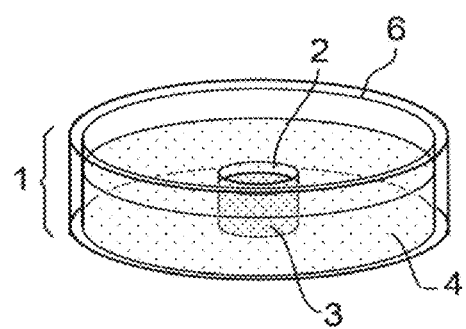
FIGS. 1a and 1b represent a perspective side view and top view respectively, of a first embodiment of the invention, in which the part comprises a Petri box that acts as a support device.

The principle on which this invention is based consists of artificially modifying the geometry of the object to be tested so as to artificially prolong the dimensions of the object to be tested by using an extension material with electrical characteristics similar to those of the object.

The material with which the extension of the volume of the OUT is made must have a relative permittivity and preferably an electrical conductivity as close as possible to those of the object to be tested, so as to form the globally most uniform possible volume. The material from which the extension element(s) is (are) made may be a composite material, a ceramic or a gel, etc.

The assembly formed by the object to be tested and its 3d extension 10 then behave like a single object. Thus, the level of the electric field induced in the object under test depends on the global dimensions of the "object to be tested+extension" assembly, and more particularly its dimensions along the direction of the electric field. Indeed, the distribution of the electric field depends on the global geometry, independently of the geometry of the object to be tested. Provided that the dimension of the object to be tested is relatively small compared with the global dimension of the "object to be tested+extension" assembly along the direction of the incident electric field (this is why the length of the extension element is, on both sides of the cavity in which the object to be tested is placed, equal to at least one third of the cavity along the passage direction), the uniformity and intensity of the field in the object to be tested is significantly improved compared with an "object to be tested alone" configuration.

In fact, the total length of the extension material along the passage direction of the cavity (lengths of the extension element(s) on each side of the cavity) can both compensate for the resulting edge non-uniformity caused, in prior art, by the walls of the container in which the object to be tested is placed and the surrounding vacuum, and also increase the coupling length with the incident electric field.

Finally, the total length of the extension material shall be chosen as a function of the required degree of improvement.

For example, in the case illustrated below for an Eppendorf™ tube, since the dimension of the cavity along the passage direction is a few centimetres, coupling between the incident electric field and the induced electric field is already significant. The extension material is then useful principally for making the induced electric field uniform and the total length of the extension material may be as low as ⅓ of the length of the cavity.

On the contrary, in the case illustrated below of a cylindrical cavity with a radius of 4 mm made in a layer deposited in a Petri box, the extension material, in addition to its role of increasing uniformity, also has the effect of increasing the coupling length. Therefore the total length of the extension material must be much longer than in the previous case. For example, in the example illustrated below there is a ratio of more than 10 between the length of the "object under test+extension material" assembly along the passage direction and the length of the cavity.

In all cases, the optimal coupling length (the "object under test+extension material" being considered like an antenna in reception) is a fraction of the incident wave length. If this length is too short, coupling will not be improved much; but if this length is too long, there is a risk of stationary waves developing within the "object under test+extension material" assembly. Therefore the one skilled in the art will have to adjust the length of the extension material depending on the required results.

Depending on the configuration of the extension element(s), it is possible to obtain an extension of the volume of the object to be tested along one direction (1D extension) (see the example of the Eppendorf™ tube below), along two directions (2D extension) (see the two examples below of a plate and a Petri box) and along three dimensions (3D extension).

The part may include a support device. This support device may be in various forms (Petri box, well plate, microscope slide, Eppendorf™ tube, etc.) and must be adapted to the specific features of experiments and the nature of objects under test, that will define the composition of the extension material (ceramic, gel, etc.). Note that the choice of the support device and the extension material must take account of various constraints on the geometry, electrical properties, mechanical and chemical properties (for example such as the resistance to sterilisation, if the support device and the extension element(s) is (are) to be reused).

In the following examples, the object to be tested is a 12.5 µL suspension containing Giant Unilammelar cells (GUV) in a solution of 1,2-dioleoyl-sn-glycero-3-phosphocholine (DOPC). The relative permittivity of the object is 73.75 and its electrical conductivity is 1.73 S/m at the frequency of 1.5 GHz. The extension element(s) is (are) made of agar agar, that has a relative permittivity of 76 and an electrical conductivity of 0.37 S/m at this frequency.

Figure 1B:
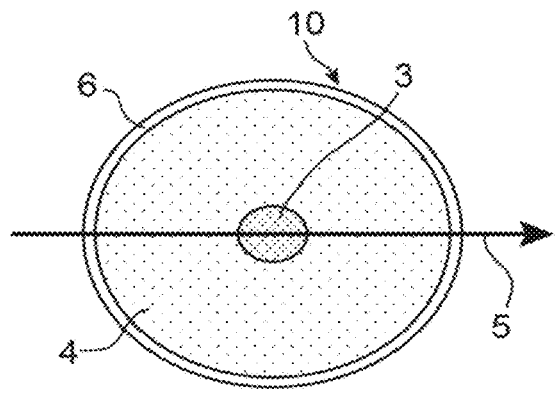

According to a first embodiment shown in FIGS. 1a and 1b, the part 1 comprises a support device 6 that is a Petri box and the extension element 4 is a layer of agar-agar deposited in the Petri box, in which a well is made that will form the cavity 2 inside which the object to be tested 3 will be located. Preferably, the well is made in the layer at the centre of the Petri box so as to maximise the length of the extension element on each side of the cavity. Thus in this representation, the layer delimits the cavity along the passage direction 5 over the entire lateral cylindrical wall of the cavity (in the plane of the layer). The circular wall forming the bottom of the cavity is formed by the support device (the Petri box). Therefore the incident electric field may be directed indifferently in the plane of the layer. The constraint on the direction of the electric field is then eliminated.

This geometry becomes compatible with the use of an incident electromagnetic wave with circular polarisation or an incident wave with elliptical polarisation, for which the direction of the electric field rotates in a plane parallel to the surface of the bottom of the Petri box.

Finally, if a Petri box is used, the volume of the object to be tested can be reduced to the volume of a disk a few millimetres thick located at the centre of a hollowed out disk formed by a layer made of a material with dielectric characteristics similar to those of the object to be tested.

Figure 2A:
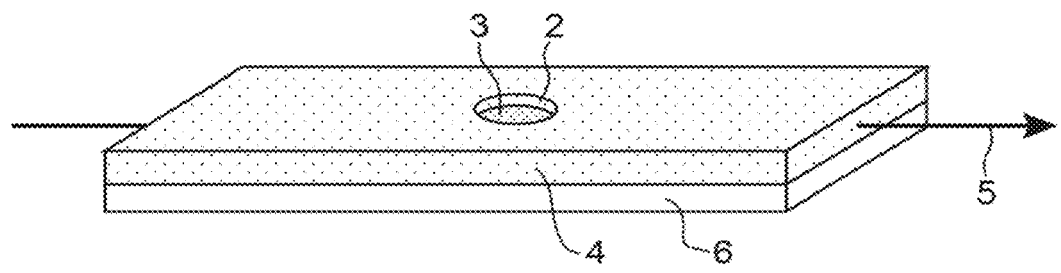
FIGS. 2a and 2b represent a perspective side view and a longitudinal sectional view respectively, of a second possible embodiment of the invention, in which the part comprises a microscope slide that acts as a support device.
Figure 2B:
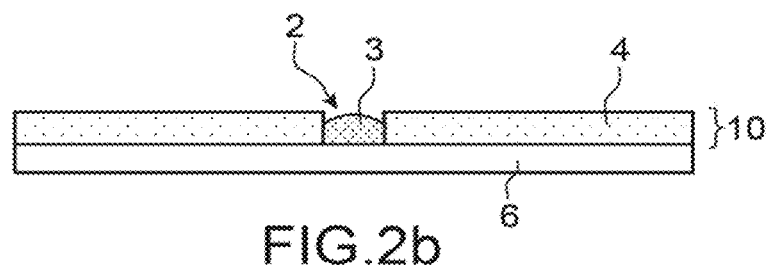

According to a second embodiment illustrated in FIGS. 2a and 2b, the part 1 comprises a support device 6 that is a standard glass microscope slide (24×80 mm), on which a 1 mm (thickness not critical) layer of agar agar is deposited. The layer also includes at its centre a cylindrical well that forms the cavity 2 for the object to be tested 3.

A glass slide can be added above the agar agar layer to make sure that the well is leak tight and to allow vertical positioning of the part during illumination by a wave with horizontal incidence, or top-down positioning during observations under a microscope.

Figure 3:
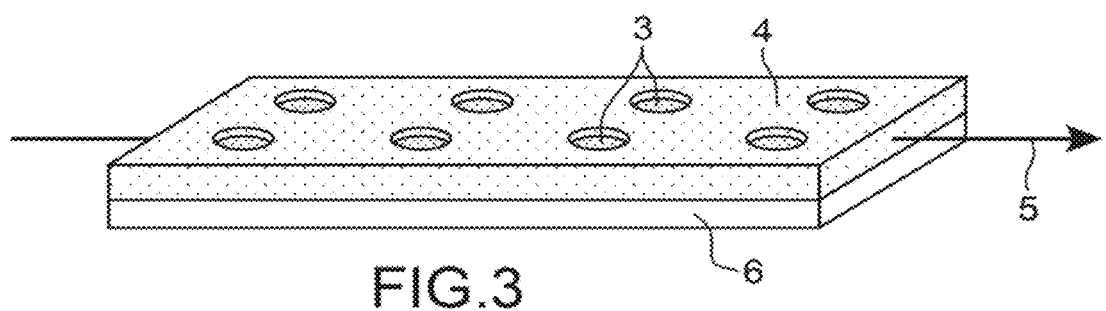
FIG. 3 represents a perspective side view of a third possible embodiment of the invention, in which the part comprises a well plate that acts as a support device.

Several wells can be made in this layer as shown in FIG. 3 that shows a third embodiment of the invention. This embodiment can be used to test several objects to be tested simultaneously.

Figure 4:
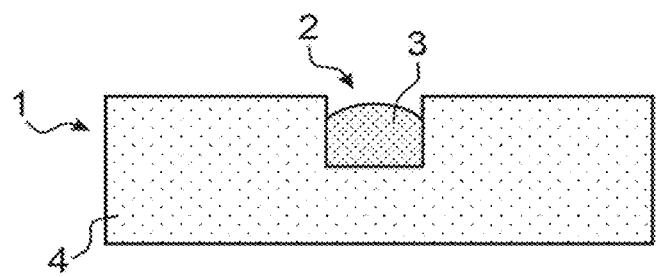
FIG. 4 represents a longitudinal sectional view of a fourth possible embodiment of the invention, in which the part does not comprise a support device and the extension element is a layer in which a non-through well is made.
Figure 5:
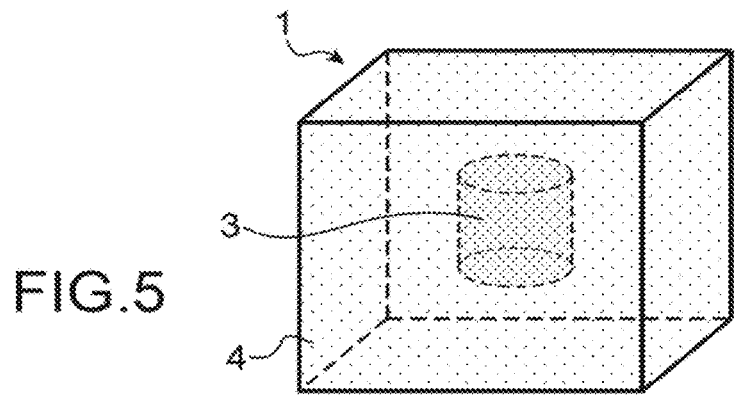
FIG. 5 represents a perspective view of a fifth possible embodiment of the invention, in which the part does not comprise a support device and the extension element is a block in which a closed well is made.

Note that the well(s) can be made in all or some of the thickness of the layer of extension material. If the layer made of an extension material is located on a support device, the well(s) can be through wells and can pass through the thickness of the layer. FIG. 4 shows a fourth embodiment that is the case for a non-through well made in a thick layer made of extension material. This configuration eliminates the need to use a support device, since the extension volume performs the twofold function of cavity and support. According to a fifth embodiment, a closed cavity can also be made inside a block made of extension material, as shown in FIG. 5. The result is that the volume of the object is extended in the three dimensions.

Figure 6:
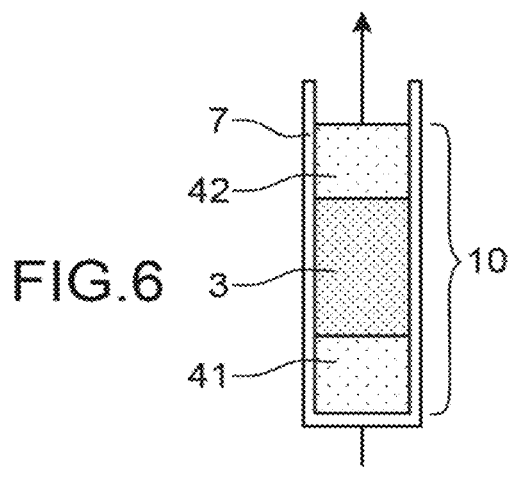
FIG. 6 represents a sixth possible embodiment of the invention, in which the part comprises an Eppendorf™ type tube that acts as a support device.
Figure 7:
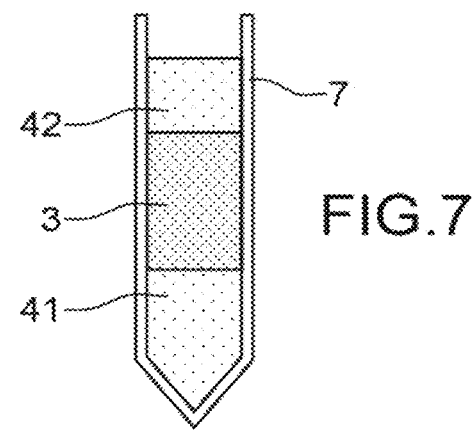
FIG. 7 represents a seventh possible embodiment of the invention, in which the part comprises an Eppendorf™ type tube with a conical shaped end that acts as a support device.
Figure 8A:
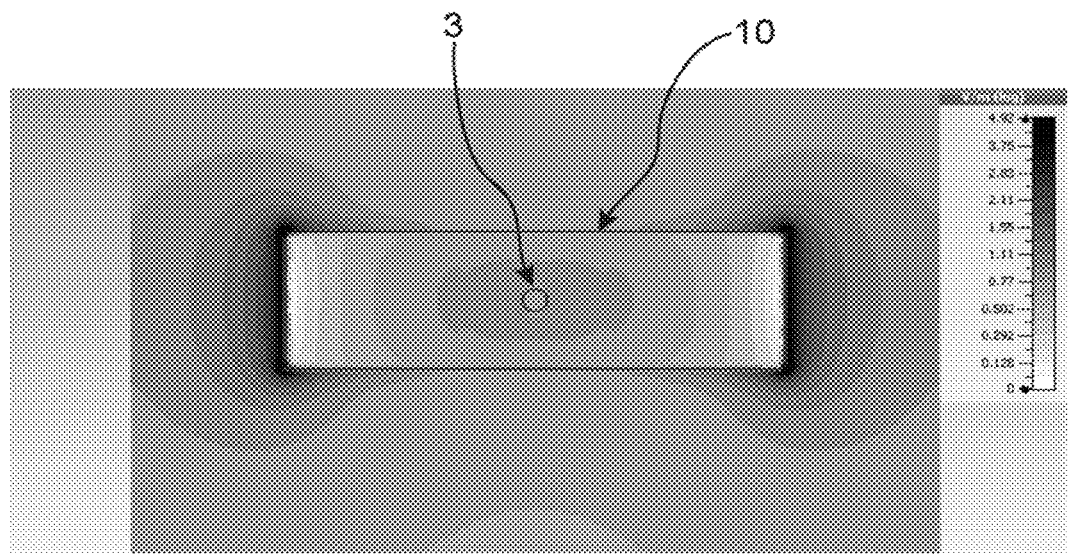
FIGS. 8a and 8b represent the map of peak electric fields (in absolute value) in a horizontal cut plane passing through the centre of the object under test, for the object under test in a particular extension element (FIG. 8a) and for the object under test alone (FIG. 8b) respectively.
Figure 8B:
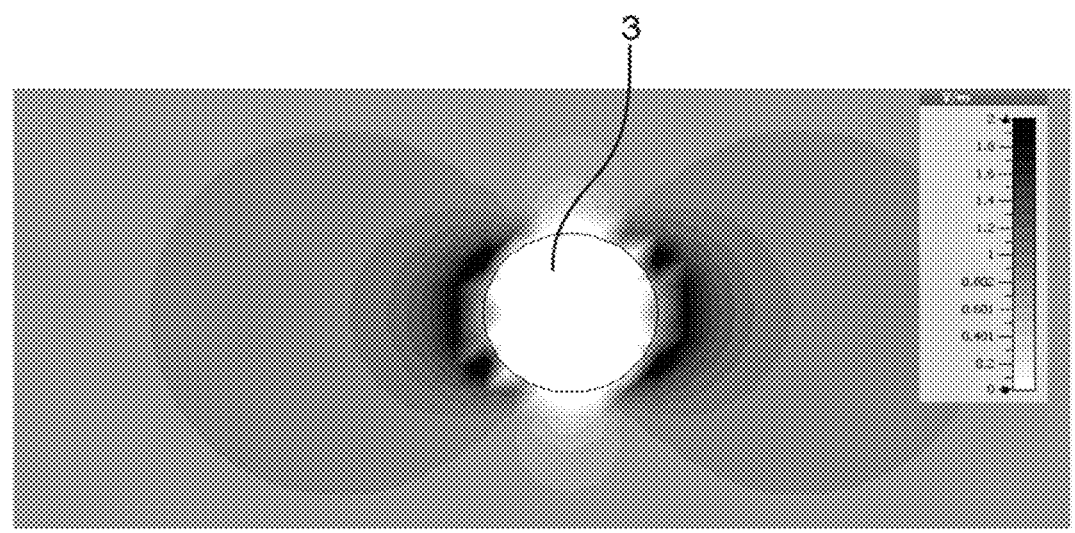
Figure 9A:
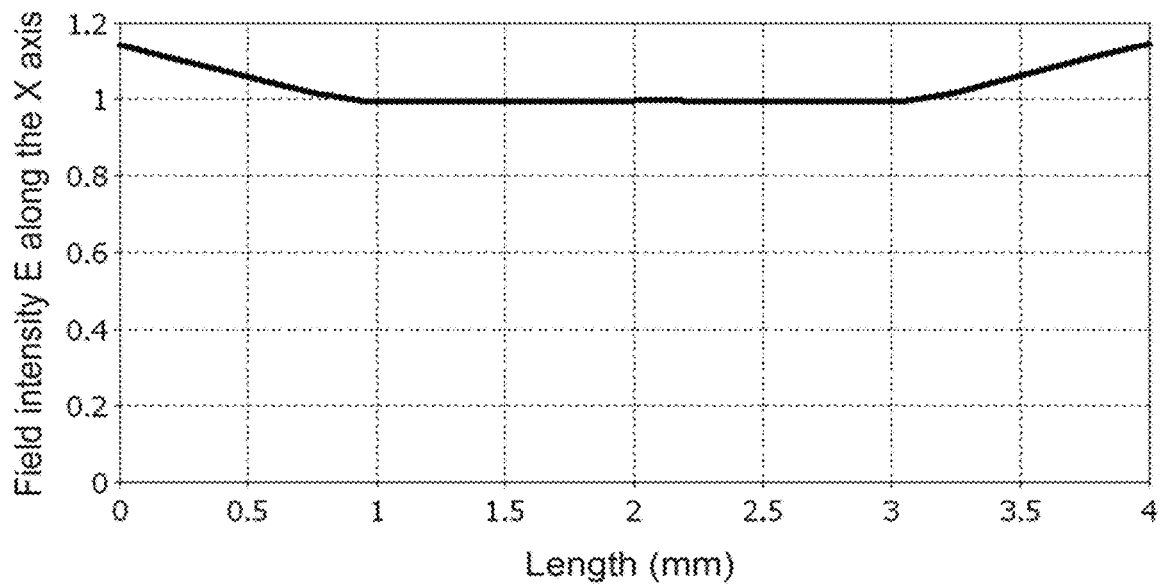
FIGS. 9a and 9b represent the associated profile read on the x axis (direction of the incident electrical field) in the object under test, for the object under test in an extension element (FIG. 9a) and for the object under test alone (FIG. 9b) respectively.
Figure 9B:
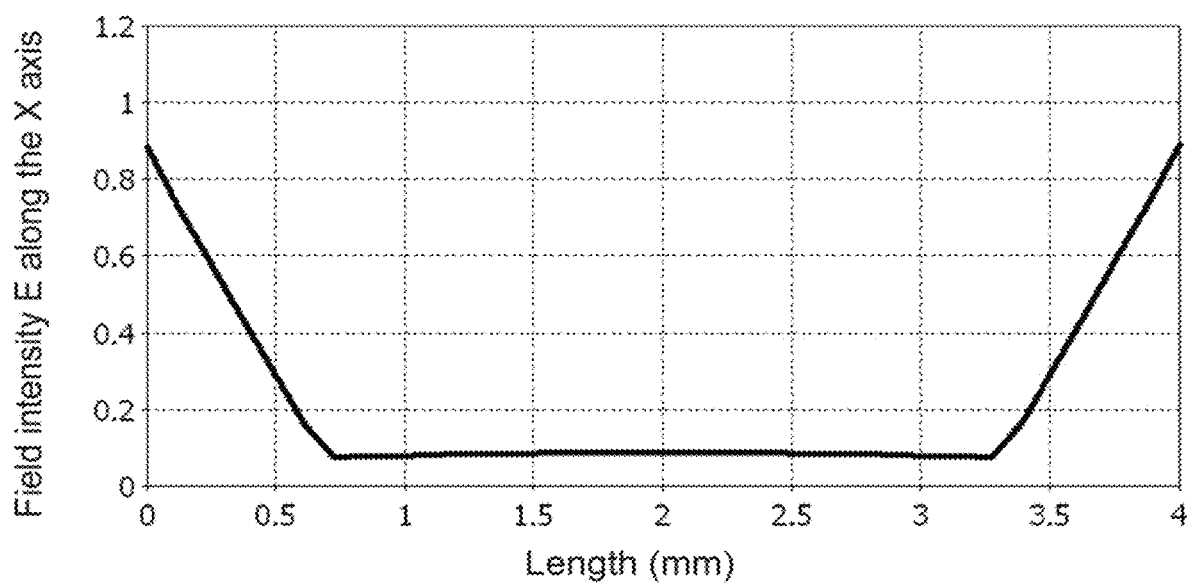
Figure 10A:
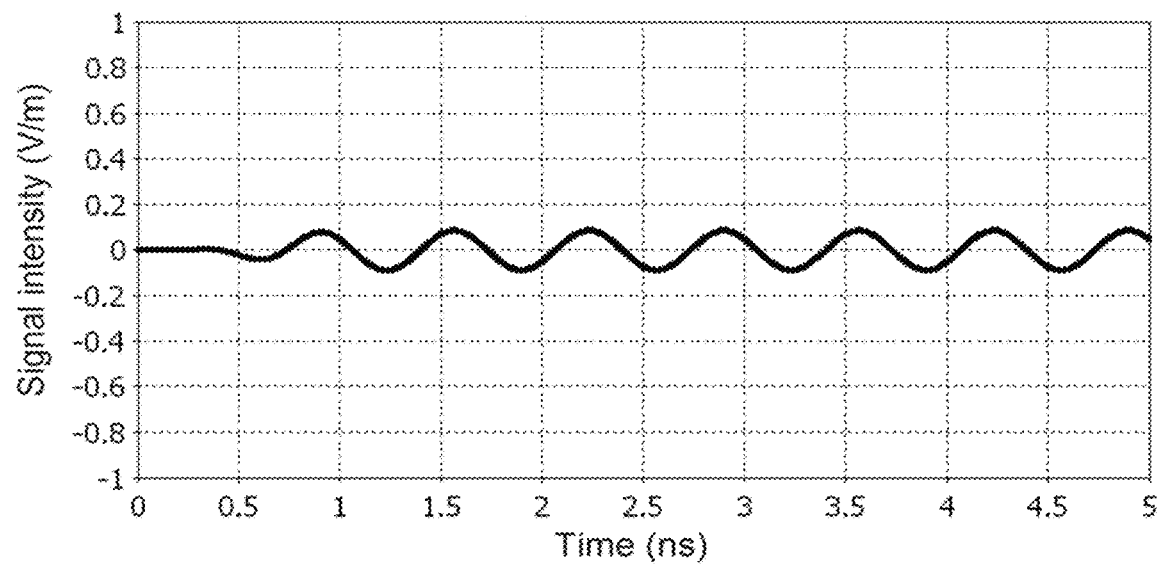
FIGS. 10a and 10b represent the variations with time of component Ex (where Ex is the component parallel to the incident electrical field) at the centre of the object under test in an extension element (FIG. 10a) and for the object under test alone (FIG. 10b), respectively.
Figure 10B:
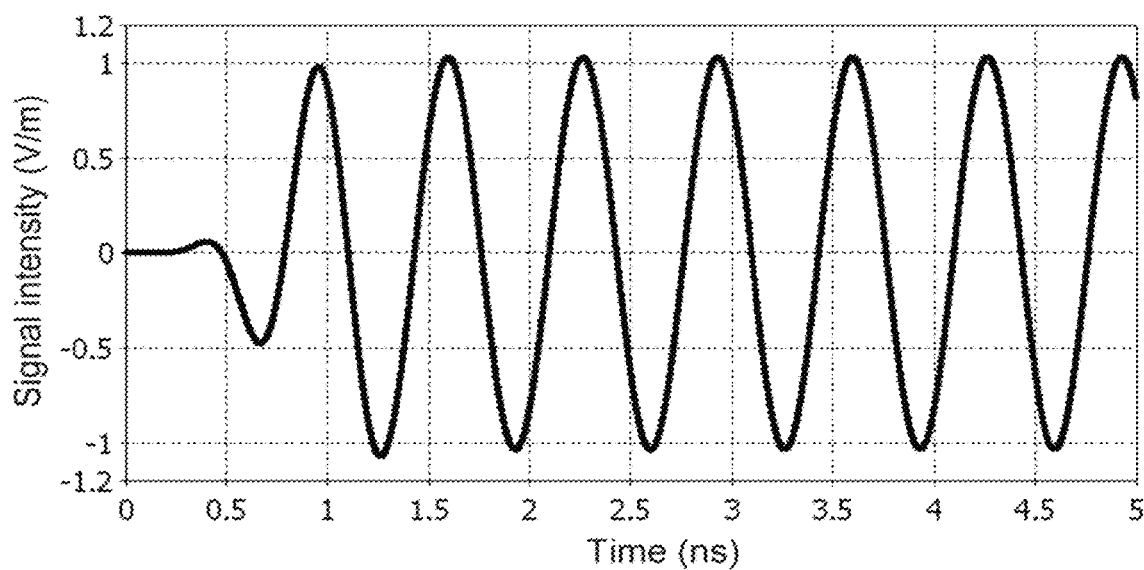

According to a sixth embodiment of the invention shown in FIG. 6, the part 1 includes a hollow support device that is a cylindrical tube such as an Eppendorf™ type tube, and the extension element is composed of two plugs 41, 42 made of agar agar, placed at the ends of the tube, the object to be tested 3 being placed in the tube between these two plugs. If a conical Eppendorf™ type tube is used (FIG. 7), this solution has the advantage that it avoids the additional non-uniformity added inside the tube by this particular geometry.

We made two digital simulations using the CST Microwave Studio software™ to illustrate the efficiency of this method according to the invention, using an object to be tested alone as the reference sample, and the same object deposited in a well made in a layer of agar agar on a microscope slide, as illustrated in FIG. 2.

The dimension of the extension material in the direction of incidence of the electric field regulates the amplitude of the electric field induced in the object to be tested.

For example, for an object to be tested in the form of a 4 mm diameter 1 mm thick disk, a relative permittivity ($\varepsilon_r$) of 80, an electrical conductivity (σ) of 1.5 S/m at a frequency of 1.5 GHz, and a 24 mm×80 mm×1 mm virtual extension material (but that could be a low loss ceramic) with a relative permittivity of 60 and zero electrical conductivity at this frequency.

A comparison between the results obtained for these two digital simulations shows the efficiency of the method according to the invention in improving the uniformity and intensity of the field.

It can be seen that the ratio between the maximum intensity of the electric field induced at the centre of the object under test and the intensity of the incident electric field varies from 10% (without extension material) to 100% (with extension material). The non-uniformity ratio varies from 800% (without extension material) to 14% (with extension material).

For illustration purposes, FIGS. 8a and 8b, 9a and 9b, 10a and 10b contain the results obtained using a plane electromagnetic wave with normal incidence, for the configuration with extension material (FIGS. 8a, 9a and 10a) and for the configuration without extension material (FIGS. 8b, 9b and 10b) respectively.

It can be seen that gains due to the use of an extension are more than an order of magnitude, both in terms of the intensity of the induced electric field and the uniformity of the electric field in the volume of the object under test, despite significant differences in permittivity and conductivity of the object under test and the extension material.

An additional digital simulation was made using the characteristics of 2% agar agar for the extension material (relative permittivity equal to 76 and electrical conductivity 0.37 S/m at a frequency of 1.5 GHz). The results obtained show a non-uniformity ratio of 5% instead of the 14% obtained with the virtual extension material considered during the previous simulation. Thus, it can be seen that the uniformity and intensity of the field induced in the object under test are further improved when using an extension material for which the relative permittivity and electrical conductivity are similar to those of the object under test.

The invention claimed is:

1. A method for improving uniformity and intensity of an electric field induced in an object to be tested illuminated by an incident electromagnetic wave, the object having a relative permittivity, wherein the method comprises:

preparing the object to be tested, the preparing comprising
supplying a part having a cavity to house the object and at least one extension element made of a material with a relative permittivity equal to the relative permittivity of the object within +/−50%, the at least one extension element partly delimiting the cavity and extending on each side of the cavity along a passage direction of the cavity, over a length which is, on each side of the cavity, equal to at least one third of the length of the cavity along the passage direction;

placing the object in the cavity such that the object is in contact with the at least one extension element along the passage direction; and placing the part in an exposure system having a hollow electrically conducting element made of an electrically conducting material extending along a longitudinal direction and having two electrically conducting portions facing each other in a section plane along the longitudinal direction, the part being placed in the hollow electrically conducting element between the two electrically conducting portions of the hollow electrically conducting element; and applying an incident electric field on the object to be tested by illumination of the object with an incident electromagnetic wave, a direction of the incident electric field of the incident electromagnetic wave being chosen to be identical to the passage direction of the cavity.

2. The method according to claim 1, wherein the at least one extension element of the part is in contact with at least one of the two electrically conducting portions.

3. The method according to claim 1, wherein the at least one extension element has a relative permittivity equal to the relative permittivity of the object within +/−40%.

4. The method according to claim 3, wherein the relative permittivity of the at least one extension element is equal to the relative permittivity of the object.

5. The method according to claim 1, wherein an electrical conductivity of the at least one extension element is equal to an electrical conductivity of the object within +/−30%.

6. The method according to claim 1, wherein the part comprises a support device and the at least one extension element is a layer deposited on a surface of the support device, a well being made in the layer to form the cavity.

7. The method according to claim 1, wherein the at least one extension element is a layer, a non-through well being made in the layer to form the cavity in which the object is to be housed.

8. The method according to claim 1, wherein the at least one extension element is a block comprising a closed cavity that forms the cavity in which the object is to be housed.

9. The method according to claim 1, wherein the part comprises a hollow support device with two opposite ends connected by a wall and the at least one extension element is a first layer closing off one of the two ends of the hollow support device and a second layer closing off the other of the two ends of the hollow support device, a space delimited by the wall and the first and second layers forming the cavity in which the object is to be housed.

10. The method according to claim 1, wherein the length of the at least one extension element on each side of the cavity is equal to at least half the length of the cavity along the passage direction.

11. A method for improving uniformity and intensity of an electric field induced in an object to be tested illuminated by an incident electromagnetic wave, the object having a relative permittivity, wherein the method comprises:

preparing the object to be tested the preparing comprising:

supplying a part having a cavity to house the object and having at least one extension element made of a material with a relative permittivity equal to the relative permittivity of the object within +/−50%, the at least one extension element partly delimiting the cavity and extending on each side of the cavity along a passage direction of the cavity, over a length which is, on each side of the cavity, equal to at least one third of the length of the cavity along the passage direction;

placing the object in the cavity such that the object s in contact with the at least one extension element along the passage direction; and placing the part in an exposure system having at least two electrically conducting elements made of an electrically conducting material and placed approximately parallel to and facing each other, such that the part s placed between the two electrical conducting elements; and applying an incident electric field on the object to be tested by illumination of the object with an incident electromagnetic wave, a direction of the incident electric field of the incident electromagnetic wave being chosen to be identical to the passage direction of the cavity.

12. The method according to claim 11, wherein the at least one extension element of the part is in contact with at least one of the two electrically conducting elements.

13. The method according to claim 11, wherein the at least one extension element has a relative permittivity equal to the relative permittivity of the object within +1-40%.

14. The method according to claim 13, wherein the relative permittivity of the at least one extension element is equal to the relative permittivity of the object.

15. The method according to claim 11, wherein an electrical conductivity, of the at least one extension element is equal to an electrical conductivity of the object within +/−30%.

16. The method according to claim 11, wherein the part comprises a support device and the at least one extension element is a layer deposited on a surface of the support device, a well being made in the layer to form the cavity.

17. The method according to claim 11, wherein the at least one extension element is a layer, a non-through well being made in the layer to form the cavity in which the object is to be housed.

18. The method according to claim 11, wherein the at least one extension element is a block comprising a closed cavity that forms the cavity in which the object is to be housed.

19. The method according to claim 11, wherein the part comprises a hollow support device with two opposite ends connected by a wall and the at least one extension element is a first layer closing off one of the two ends of the hollow support device and a second layer closing off the other of the two ends of the hollow support device, a space delimited by the wall and the first and second layers forming the cavity in which the object is to be housed.

20. The method according to claim 11, wherein the length of the at least one extension element on each side of the cavity is equal to at least half the length of the cavity along the passage direction.

* * * * *

UNITED STATES PATENT AND TRADEMARK OFFICE
CERTIFICATE OF CORRECTION

PATENT NO. : 10,690,710 B2
APPLICATION NO. : 15/312867
DATED : June 23, 2020
INVENTOR(S) : Rene Vezinet et al.

Page 1 of 1

It is certified that error appears in the above-identified patent and that said Letters Patent is hereby corrected as shown below:

On the Title Page

Item (72), the third inventor's name is incorrect. Item (72) should read:
-- (72) Inventors: Rene Vezinet, Bio (FR); Alexandre Catrain, Le Vigan (FR); Thomas Chretiennot, Gramat (FR) --

Signed and Sealed this
First Day of September, 2020

Andrei Iancu
*Director of the United States Patent and Trademark Office*